US007162294B2

(12) United States Patent
Rowlandson et al.

(10) Patent No.: US 7,162,294 B2
(45) Date of Patent: Jan. 9, 2007

(54) SYSTEM AND METHOD FOR CORRELATING SLEEP APNEA AND SUDDEN CARDIAC DEATH

(75) Inventors: G. Ian Rowlandson, Milwaukee, WI (US); David E. Albert, Oklahoma City, OK (US); Patrick Dorsey, Menomonee Falls, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 387 days.

(21) Appl. No.: 10/825,381

(22) Filed: Apr. 15, 2004

(65) Prior Publication Data

US 2005/0234313 A1 Oct. 20, 2005

(51) Int. Cl.
*A61B 5/04* (2006.01)
(52) U.S. Cl. ..................................... 600/513
(58) Field of Classification Search .............. None
See application file for complete search history.

(56) References Cited

U.S. PATENT DOCUMENTS

| | | | |
|---|---|---|---|
| 3,554,187 A | 1/1971 | Glassner et al. |
| 3,658,055 A | 4/1972 | Abe et al. |
| 3,759,248 A | 9/1973 | Valiquette |
| 3,821,948 A | 7/1974 | King |
| 3,902,479 A | 9/1975 | Chaumet |
| 3,952,731 A | 4/1976 | Worstencroft |
| 4,124,894 A | 11/1978 | Vick et al. |
| 4,136,690 A | 1/1979 | Anderson et al. |
| 4,170,992 A | 10/1979 | Dillman |
| 4,181,135 A | 1/1980 | Andresen et al. |
| 4,202,340 A | 5/1980 | Langer et al. |
| 4,316,249 A | 2/1982 | Gallant et al. |
| 4,417,306 A | 11/1983 | Citron et al. |
| 4,422,459 A | 12/1983 | Simson |
| 4,432,375 A | 2/1984 | Angel et al. |
| 4,457,315 A | 7/1984 | Bennish |
| 4,458,691 A | 7/1984 | Netravali |
| 4,458,692 A | 7/1984 | Simson |
| 4,475,558 A | 10/1984 | Brock |
| 4,492,235 A | 1/1985 | Sitrick |
| 4,519,395 A | 5/1985 | Hrushesky |
| 4,583,553 A | 4/1986 | Shah et al. |
| 4,589,420 A | 5/1986 | Adams et al. |
| 4,603,703 A | 8/1986 | McGill et al. |
| 4,616,659 A | 10/1986 | Prezas et al. |

(Continued)

FOREIGN PATENT DOCUMENTS

DE 2604460 8/1977

(Continued)

OTHER PUBLICATIONS

Tateishi et al, "Observation of sleep-related breathing disorders in patients with coronary artery disease by ambulatory electrocardiogram-respiration monitoring system", Japan Circulation Journal, Nov. 1994; 58 (11), pp. 831-835.*

(Continued)

*Primary Examiner*—Carl Layno
(74) *Attorney, Agent, or Firm*—Andrus, Sceales, Starke & Sawall, LLP

(57) ABSTRACT

A system and method for determining a correlation between sleep apnea and sudden cardiac death. One embodiment of the method can include predicting sudden cardiac death in a patient being monitored for sleep apnea by acquiring respiration data and electrocardiogram data from the patient and analyzing the respiration data and the electrocardiogram data to determine a correlation between sleep apnea and sudden cardiac death.

27 Claims, 3 Drawing Sheets

U.S. PATENT DOCUMENTS

| | | | |
|---|---|---|---|
| 4,665,485 A | 5/1987 | Lundy et al. | |
| 4,679,144 A | 7/1987 | Cox et al. | |
| 4,680,708 A | 7/1987 | Ambos et al. | |
| 4,732,157 A | 3/1988 | Kaplan et al. | |
| 4,796,638 A | 1/1989 | Sasaki | |
| 4,802,491 A | 2/1989 | Cohen et al. | |
| 4,832,038 A | 5/1989 | Arai et al. | |
| 4,854,327 A | 8/1989 | Kunig | |
| 4,860,762 A | 8/1989 | Heumann et al. | |
| 4,896,677 A | 1/1990 | Kaneko et al. | |
| 4,924,875 A | 5/1990 | Chamoun | |
| 4,928,690 A | 5/1990 | Heilman et al. | |
| 4,938,228 A | 7/1990 | Righter et al. | |
| 4,951,680 A | 8/1990 | Kirk et al. | |
| 4,955,382 A | 9/1990 | Franz et al. | |
| 4,957,115 A | 9/1990 | Selker | |
| 4,958,641 A | 9/1990 | Digby et al. | |
| 4,972,834 A | 11/1990 | Begemann et al. | |
| 4,974,162 A | 11/1990 | Siegel et al. | |
| 4,974,598 A | 12/1990 | John | |
| 4,977,899 A | 12/1990 | Digby et al. | |
| 4,979,510 A | 12/1990 | Franz et al. | |
| 4,989,610 A | 2/1991 | Patton et al. | |
| 4,998,535 A | 3/1991 | Selker et al. | |
| 5,000,189 A | 3/1991 | Throne et al. | |
| 5,010,888 A | 4/1991 | Jadvar et al. | |
| 5,020,540 A | 6/1991 | Chamoun | |
| 5,025,795 A | 6/1991 | Kunig | |
| 5,042,497 A | 8/1991 | Shapland | |
| 5,092,341 A | 3/1992 | Kelen | |
| 5,109,862 A | 5/1992 | Kelen et al. | |
| 5,117,833 A | 6/1992 | Albert et al. | |
| 5,117,834 A | 6/1992 | Kroll et al. | |
| 5,148,812 A | 9/1992 | Verrier et al. | |
| 5,187,657 A * | 2/1993 | Forbes | 600/513 |
| 5,188,116 A | 2/1993 | Pommrehn et al. | |
| 5,201,321 A | 4/1993 | Fulton | |
| 5,234,404 A | 8/1993 | Tuttle et al. | |
| 5,253,650 A | 10/1993 | Wada | |
| 5,265,617 A | 11/1993 | Verrier et al. | |
| 5,276,612 A | 1/1994 | Selker | |
| 5,277,188 A | 1/1994 | Selker | |
| 5,277,190 A | 1/1994 | Moulton | |
| 5,323,783 A | 6/1994 | Henkin et al. | |
| 5,343,870 A | 9/1994 | Gallant et al. | |
| 5,423,878 A | 6/1995 | Franz | |
| 5,437,285 A | 8/1995 | Verrier et al. | |
| 5,501,229 A | 3/1996 | Selker et al. | |
| 5,560,370 A | 10/1996 | Verrier et al. | |
| 5,570,696 A | 11/1996 | Arnold et al. | |
| 5,718,233 A | 2/1998 | Selker et al. | |
| 5,724,983 A | 3/1998 | Selker et al. | |
| 5,747,274 A | 5/1998 | Jackowski | |
| 5,819,007 A | 10/1998 | Elghazzawi | |
| 5,819,741 A | 10/1998 | Karlsson et al. | |
| 5,902,250 A * | 5/1999 | Verrier et al. | 600/515 |
| 5,921,940 A | 7/1999 | Verrier et al. | |
| 5,935,082 A | 8/1999 | Albrecht et al. | |
| 6,059,724 A | 5/2000 | Campell et al. | |
| 6,067,466 A | 5/2000 | Selker et al. | |
| 6,099,469 A | 8/2000 | Armstrong et al. | |
| 6,142,078 A | 11/2000 | Lachajewski | |
| 6,169,919 B1 | 1/2001 | Nearing et al. | |
| 6,334,192 B1 | 12/2001 | Karpf | |
| 6,370,423 B1 * | 4/2002 | Guerrero et al. | 600/513 |
| 6,394,952 B1 | 5/2002 | Anderson et al. | |
| 6,443,889 B1 | 9/2002 | Groth et al. | |
| 6,450,954 B1 | 9/2002 | Selker | |
| 6,453,191 B1 | 9/2002 | Krishnamachari | |
| 6,507,753 B1 | 1/2003 | Xue et al. | |

| | | | |
|---|---|---|---|
| 2004/0215258 A1 * | 10/2004 | Lovett et al. | 607/9 |

FOREIGN PATENT DOCUMENTS

| | | |
|---|---|---|
| DE | 3303104 | 8/1984 |
| DE | 4024360 | 3/1991 |
| EP | 0080821 | 6/1983 |
| FR | 2539978 | 8/1984 |
| GB | 2070871 | 9/1981 |
| WO | WO81/02832 | 10/1981 |

OTHER PUBLICATIONS

Richard S. T. Leung and T. Douglas Bradley, Sleep Apnea and Cardoivascular Disease, Am J Respir Crit Care Med, vol. 164, pp. 2147-2165, 2001, www.atsjournals.org.

Don D. Sin, Fabia Fitzgerald, John D. Parker, Gary Newton, John S. Floras and T. Douglas Bradley; Risk Factors for Central and Obstructive Sleep Apnea in 450 Men and Women with Congestive Heart Failure; Am J Respir Crit Care Med, vol. 160, pp. 1101-1106, 1999, www.atsjournals.org.

Jack J. Salah, M.D., Central Sleep Apnea in Chronic Congestive Heart Failure: Update and Implications for Management; Jacksonville Medicine, http://www.dcmsonline.org/jax-medicine/2001journals/March2001/sleepapnea.htm, Mar. 2001.

John D. Zoidis, M.D., Heart Failure and CPAP: A Review of the Evidence; Sleep Review, http://www.sleepreviewmag.com/articles.ASP?ArticleID=S0301F03, Jan./Feb. 2003.

Major Improvement in Heart Function Shown by Treating Sleep Disorder; Mount Sinai Hospital news release, Toronto General Hospital, Toronto Rehab, Mar. 27, 2003.

Heavy Breathing in the Night: Central Sleep Apnea in Heart Failure; http://www.upenn.edu/researchatpenn/article.php?217&hlt, Sep. 26, 2001.

Congestive Heart Failure, Jun. 2002.

Ryan, et al.; ACC/AHA Guidelines for the Management of Patients With Acute Myocardial Infarction; Journal of the American College of Cardiology; vol. 28, No. 5, Nov. 1, 1996; 1328-428.

Ryan, et al.; 1999 Update: ACC/AHA Guidelines for the Management of Patients With Acute Myocardial Infarction; Journal of the American College of Cardiology; Vol. 34, No. 3, Sep. 1999; 890-911.

Circulation; American Heart Association; ECC Guidelines, Part 7: The Era of Reperfusion; http://circ.ahajournals.org/cgi/content/full/102/suppl_1/I-172?maxtoshow+HIRA=10&hits=10&RES; 2000; 102: I-172.

Kudenchuk, et al., Accuracy of Computer-Interpreted Electrocardiography in Selecting Patients for Thrombolytic Therapy; Journal of the American College of Cardiology; vol. 17, No. 7, Jun. 1991, 1486-91.

O'Rourke, et al.; Accuracy of a Portable Interpretive ECG Machine in Diagnosis of Acute Evolving Myocardial Infarction; Aust NZ J Med 1992; 22; 9-13.

Braunwald, et al.; ACC/AHA Guidelines for the Management of Patients With Unstable Angina and Non-ST-Segment Elevation Myocardial Infarction, Journal of the American College of Cardiology; vol. 36, No. 3, Sep. 2000; 970-1062.

Speranza et al., 'Beat-to-beat measurement and analysis of the R-T interval in 24 h ECG Holter recordings,' Med and Biol Eng & Comput, 1993, 31, pp. 487-494.

Narayanaswamy et al., 'Selective beat signal averaging and spectral analysis of beat intervals to determine the mechanisms of premature ventricular contractions,' University of Oklahoma Health Sciences Center, May 1993, pp. 81-84.

Laks et al., 'ECG computer program developed for a retrospective and prospective study of the Pardee T wave,' Department of Medicine, UCLA School of Medicine, Harbor-UCLA Medical Center, Torrence, CA, 1992, pp. 365-368.

Makarov et al., 'Holter monitoring in the long QT syndrome of children and adolescents,' Cor Vasa, 1990, 32(6), pp. 474-483.

Navarro-Lopez et al., 'Isolated T wave alternans elicited by hypocalcernia in dogs,' Electrocardiology, 1978, 11(2), pp. 103-108.

Little et al., 'Torsade de Pointes and T-U wave alternans associated with arsenic poisoning,' Pace, 1990, 13, pp. 164-170.

Weintraub et al., 'The cogenital long QT syndromes in childhood,' Journal of the American College of Cardiology, Sep. 1990, 16(3), pp. 674-680.

Bibler et al., 'Recurrent ventricular tachycardia due to pentamidine-induced cardiotoxicity,' Chest, Dec. 1988, 94(6), pp. 1303-1306.

Ahnve et al., 'Circadian variations in cardiovascular parameters during sleep deprivation, A noninvasive study of young healthy men,' European Journal of Applied Physiology, 1981, 46, pp. 9-19.

Surawicz, 'ST-segment, T-wave, and U-wave changes during myocardial ischmeia and after infarction,' Canadian Journal of Cardiology, Supplement A, Jul. 1986, pp. 71A-84A.

Stroobandt et al., 'Simultaneous recording of atrial and ventricular monophasic action potentials: monophasic action potential duration during atrial pacing, ventricular pacing, and ventricular fibrillation,' Jul.-Aug. 1985, 8, pp. 502-511.

Sharma et al., 'Romano-Ward prolonged QT syndrome with intermittant T wave alternans and atrioventricular block,' American Heart Journal, 1981, pp. 500-501.

Navarro-Lopez et al., 'Isolated T Wave alternans,' American Heart Journal, 1978, pp. 369-374.

Mitsutake et al., 'Usefulness of the Valsalva Maneuver in management of the long QT syndrome,' Circulation, 1981, 63(5), pp. 1029-1035.

Nearing et al., 'Personal computer system for tracking cardiac vulnerability by complex demodulation of the T wave,' American Physiological Society, 1993, pp. 2606-2612.

Joyal et al., 'ST-segment alternans during percutaneous transluminal coronary angioplasty,' Division of Cardiology, Department of Medicine, University of Florida and the Veterans Administration Medical Center, Jun. 1984, pp. 915-916.

Schwartz et al., 'Electrical alternation of the T-wave: clinical and experimental evidence of it relationship with the sympathetic nervous system and with the long Q-T syndrome,' American Heart Journal, Jan. 1975, 89(1), pp. 45-50.

Schwartz, 'Idiopathic long QT syndrome: progress and questions,' American Heart Journal, Feb. 1985, 109(2), pp. 399-411.

Verrier et al., 'Electrophysiologic basis for T wave alternans as an index of vulnerability to ventricular fibrillation,' Journal of Cardiovascular Electrophysiology, May 1994, 5(5), pp. 445-461.

Verrier et al., 'Behavioral states and sudden cardiac death,' Pace, Sep. 1992, 15, pp. 1387-1393.

Turitto et al., 'Alternans of the ST segment in variant angina,' Chest, Mar. 1988, 93(3), pp. 587-591.

Ring et al., 'Exercise-induced ST segment alternans,' American Heart Journal, May 1986, 111(5), pp. 1009-1011.

Wayne et al., 'Exercise-induced ST segment alternans,' Chest, May 1983, 83(5), pp. 824-825.

Verrier et al., 'Ambulatory electrocardiogram-based tracking of T wave alternans in postmyocardial infarction patients to assess risk of cardiac arrest or arrhythmic death,' Journal of Cardiovascular Electrophysiology, Jul. 2003, 14(7), pp. 705-711.

* cited by examiner

SYSTEM AND METHOD FOR CORRELATING SLEEP APNEA AND SUDDEN CARDIAC DEATH

BACKGROUND OF THE INVENTION

Sudden cardiac death ("SCD") can be generally defined as death within one hour of the onset of symptoms without a previously-known disease or a disease that was expected to be lethal. SCD can also occur without symptoms or warnings signs. SCD is often described with respect to an unwitnessed death with the victim having been known to be alive less than 24 hours earlier.

SCD can kill its victims within minutes and often occurs in outwardly healthy people who have no known heart disease. Although it may occur in outwardly healthy people, most victims do have heart disease or other health problems, often without being aware of it. SCD claims about 300,000 lives a year in the United States and presents a public health challenge in that often the only indication a patient is at risk appears when the patient succumbs, without warning, to a heart failure episode.

In many cases, SCD victims suffer from ventricular tachycardia that degenerates into ventricular fibrillation. Ventricular tachycardia is a type of cardiac arrhythmia that is a serious, often-times, fatal condition characterized by rapid, uncontrolled, and ineffective beating of the heart. Ventricular fibrillation is a chaotic ventricular heart rhythm which produces little or no net blood flow from the heart, such that there is little or no net blood flow to the brain and other organs. Ventricular fibrillation, if not terminated, results in death. Researchers continue their efforts to predict the onset and triggers for such ventricular tachyarrhythmias and SCD.

Sleep apnea is a condition that can cause serious medical problems if left untreated. The risk of heart disease and stroke increases, and the probability of having traffic accidents also increases. Patients most likely to develop sleep apnea include those who snore loudly, are overweight, have high blood pressure, or have some physical abnormality in the nose, throat, or other parts of the upper airway.

Sleep apnea is a breathing disorder characterized by brief interruptions of breathing during sleep. There are two types of sleep apnea: central and obstructive. Central sleep apnea occurs when the brain fails to send the appropriate signals to the breathing muscles to initiate respiration. Obstructive sleep apnea occurs when air cannot flow into or out of the patient's nose or mouth although efforts to breathe continue.

Sleep apnea is thought to be caused by certain mechanical and structural problems in the airway which cause the interruptions in breathing during sleep. In some patients, sleep apnea occurs when the throat muscles and tongue relax during sleep and partially block the opening of the airway, making breathing labored and noisy, and even stopping breathing altogether. With a narrowed airway, the patient continues his efforts to breathe, but air cannot easily flow into or out of the nose or mouth. Unknown to the patient, this results in heavy snoring, periods of no breathing, and frequent arousals, which are abrupt changes from deep sleep to light sleep. During an apneic event, the patient is unable to breathe in oxygen and to exhale carbon dioxide, resulting in low levels of oxygen and increased levels of carbon dioxide in the blood. The reduction in oxygen and increase in carbon dioxide alert the brain to resume breathing and cause an arousal. With each arousal, a signal is sent from the brain to the upper airway muscles to open the airway, and breathing is resumed, but often with a loud snort or gasp.

In normal sleep, the body transitions from wakefulness to non-rapid eye movement. During this phase, there is a reduction in central respiratory drive. This results in a regular pattern of breathing. At approximately the same time, the patient's heart rate, blood pressure, stroke volume, cardiac output, and systemic vascular resistance all decrease. This results in a state of hemodynamic and autonomic relaxation during which myocardial workload is reduced. A patient with sleep apnea does not experience a regular pattern of breathing, and as a result, the body has different hemodynamic and cardiovascular responses.

BRIEF DESCRIPTION OF THE INVENTION

As the underlying physiological causes of cardiac arrhythmias are not fully understood, the effects of sleep apnea on SCD currently cannot be accurately predicted.

In one embodiment, the invention includes a method of predicting sudden cardiac death in a patient being monitored for sleep apnea. The method can include acquiring respiration and electrocardiogram data from the patient and analyzing the acquired data to determine a correlation between sleep apnea and sudden cardiac death.

DETAILED DESCRIPTION

Figure 1:
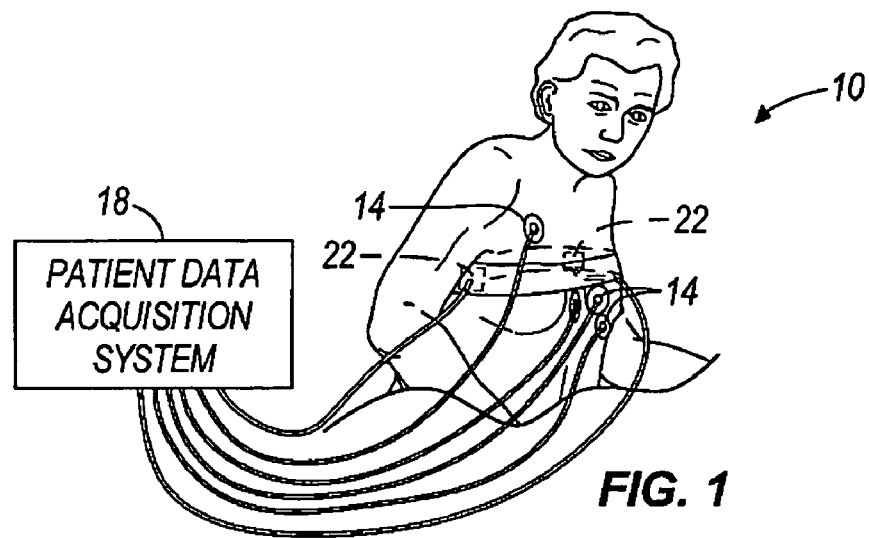
FIG. 1 illustrates a patient with electrodes connected to a patient data acquisition system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Sleep apnea and SCD are thought to be related. A patient with sleep apnea experiences oscillations between apneic and ventilatory phases with resulting changes in hemodynamic and cardiovascular parameters. Generally, after an apneic event, the patient experiences surges in heart rate and blood pressure. With multiple apneic events, the repetitive surges in hemodynamic and cardiovascular parameters prevent the normal decrease in heart rate and blood pressure that occurs in a patient without sleep apnea. These sudden changes in the hemodynamic and cardiovascular parameters may contribute to adverse cardiovascular outcomes.

Sleep apnea can be a symptom of congestive heart failure. Sleep apnea can also exacerbate congestive heart failure. Congestive heart failure is a condition or process, in which the heart is unable to pump enough blood to meet the needs of the body's tissues. Rather, the heart weakens, usually over time, so that it is unable to effectively pump out all the blood that enters its chambers. As a result, fluids tend to build up in the lungs and tissues, causing congestion. Thus, it is beneficial to monitor a patient for sleep apnea because the detection of sleep apnea can help to diagnose whether a patient has cardiac problems. In general, patients suffering from sleep apnea may be more likely to die from SCD.

Respiration can be measured and sleep apnea can be detected through various means, such as, but not limited to, impedance measurements, acoustic measurements, thermal measurements, and gas analysis measurements. Respiration can be detected via impedance measurements by applying electrodes to the chest. When the chest expands and contracts during breathing, the chest's movement causes a change in the signal between the electrodes, which a monitor senses. Respiration can be detected via acoustic measurements by attaching a microphone and associated circuitry to the patient to listen and detect respiratory sounds. Thermal measurements can be used to detect respiration by positioning a sensor or probe in the patient's mouth or placing a mask over the patient's mouth and nose to detect the temperature of air flow. Gas analysis measurements can be used to detect respiration by positioning a sensor or probe in the patient's mouth or placing a mask over the patient's mouth and nose to measure the amount of carbon dioxide being exhaled. Based on the acquired respiration data from any one or more of these measurement techniques, medical personnel can determine if a patient has sleep apnea.

FIG. 1 illustrates a patient 10 with electrocardiogram ("ECG") electrodes 14 connected to the patient's chest. The ECG electrodes 14 can be connected to a patient data acquisition system 18 that acquires and records the patient's ECG and other patient data. One or more ECG electrodes 14 can be positioned on the patient's chest to acquire an ECG. The patient data acquisition system 18 can be any suitable data acquisition, analysis, and/or storage device, such as a patient monitor or a Holter monitor. The patient data acquisition system 18 can be included in a portable housing that can be worn by the patient.

FIG. 1 also illustrates the patient 10 with respiration electrodes 22 connected to the patient's chest. The respiration electrodes 22 can be connected to the patient data acquisition system 18 that acquires and records respiration-related data for the patient 10. The respiration-related data can also be acquired through the ECG electrodes 14. The other methods of acquiring respiration data discussed above may also be used or alternatively be used, but are not illustrated or further described herein.

An ECG is a noninvasive procedure that records the electrical activity of the heart. The electrical activity is related to the impulses that travel through the heart that determine the heart's rate and rhythm. An ECG can be used to evaluate the patient's cardiac condition and indirectly determine if a heart attack has occurred; what part of the heart is damaged; if there are any irregular heart beats or rhythms; and if there is a decreased supply of blood and oxygen to the heart.

The ECG and respiration data can be acquired from the patient in various settings, such as a hospital (e.g., cardiac catheterization lab, an electrophysiology lab, an emergency room, etc.), a clinic, a sleep laboratory, or a doctor's office. The patient 10 can also be remotely monitored while at home for a longer period of time with various remote monitoring techniques, such as with a Holter monitor. In one embodiment, the patient data acquisition system 18 is a Holter monitor that can acquire impedance, acoustic, thermal, and/or gas analysis respiration measurements, along with various typical ECG or other cardiac measurements. For example, in one embodiment, the patient data acquisition system 18 can acquire impedance respiration measurements with respiration electrodes 22 and one or more channels of ECG data with ECG electrodes 14. The patient data acquisition system 18 can include one or more data storage devices. In some embodiments, the patient data acquisition system 18 can also include data analysis components and/or a display device for at-home monitoring.

The ECG measurements discussed below can be made with data acquired using the patient data acquisition system 18, for example in the form of a Holter monitor according to one embodiment of the invention. Heart rate variability ("HRV") is generally defined as the beat-to-beat variance in sinus cycle length over a period of time. A patient exhibiting low HRV shows a significantly increased risk of sudden cardiac death. Heart rate turbulence is generally defined as the physiological, bi-phasic response of the sinus node to premature ventricular contractions. Heart rate turbulence consists of a short initial acceleration followed by a deceleration of the heart rate. Heart rate turbulence can be quantified by two numerical parameters, the Turbulence Onset and the Turbulence Slope. The premature ventricular contraction causes a brief disturbance of the arterial blood pressure (low amplitude of the premature beat, high amplitude of the ensuing normal beat). When the autonomic control system is intact, this fleeting change is registered immediately with an instantaneous response in the form of heart rate turbulence. If the autonomic control system is impaired, this reaction is either weakened or entirely missing. QRS duration is generally a time series and/or waveform morphology measurement. ST/T measurements monitor the elevation or depression of the S-T segment of the ECG to determine the amount of oxygenated blood being pumped to the heart. Signal averaged ECG ("SAECG") is a technique involving computerized analysis of small segments of a standard ECG in order to detect abnormalities, termed ventricular late potentials ("VLP"), that would be otherwise obscured by "background" skeletal muscle activity. VLPs reflect aberrant, asynchronous electrical impulses arising from viable isolated cardiac muscle bordering an infarcted area and are thought to be responsible for ventricular tachyarrhythmias. T-wave alternans are generally defined as a "beat-to-beat" alternation in the T-wave portion of a patient's ECG. These alternations have been associated with an increased likelihood of ventricular arrhythmia.

Chronic and intermittent atrial fibrillation is generally a rhythm disturbance of the atria that results in irregular, chaotic, ventricular waveforms varying from bradyarrhythmia to tachyarrhythmia. Atrial fibrillation occurs when the atria beat (quivers) faster than the rest of the heart. As a result, blood is not pumped completely out of the atria, so it may pool and clot. A stroke can result if a blood clot in the atria leaves the heart and becomes lodged in an artery in the brain.

In addition to ECG and respiratory data acquired with the patient data acquisition system 18, the patient 10 may undergo other cardiology tests, such as a stress test, a stress-echo test, a stress-nuclear test, a cardiac catheterization (also known as an angiogram), an electrophysiology study, and/or other medical test procedures. Generally, these tests produce various images, results, and reports, but are not necessarily correlated to other ECG or respiratory data acquired while the patient 10 is sleeping. Some of these tests can provide cardiac measurements, such as ejection fraction, wall motion abnormalities, heart rate variability, heart rate turbulence, QRS duration, signal averaged ECG, rhythm abnormalities, T-wave alternans, ST/T measurements, intermittent or chronic atrial fibrillation, etc. Any one or combination of these measurements can be used to predict SCD, and thus each test can provide an independent indication of SCD. Generally, one test does not provide all of the measurements mentioned above and the patient does not undergo all of the tests. The medical personnel reviews the images, results, and reports of the particular test(s) that the patient 10 has undergone to provide a diagnosis and a treatment plan for the patient. Generally, the data acquired from these various cardiology tests is stored in a database and/or printed onto paper and saved in the patient's paper file. In one embodiment of the invention, the data acquired from these cardiology tests is correlated to ECG and respiratory data acquired when the patient 10 is sleeping.

Figure 2:
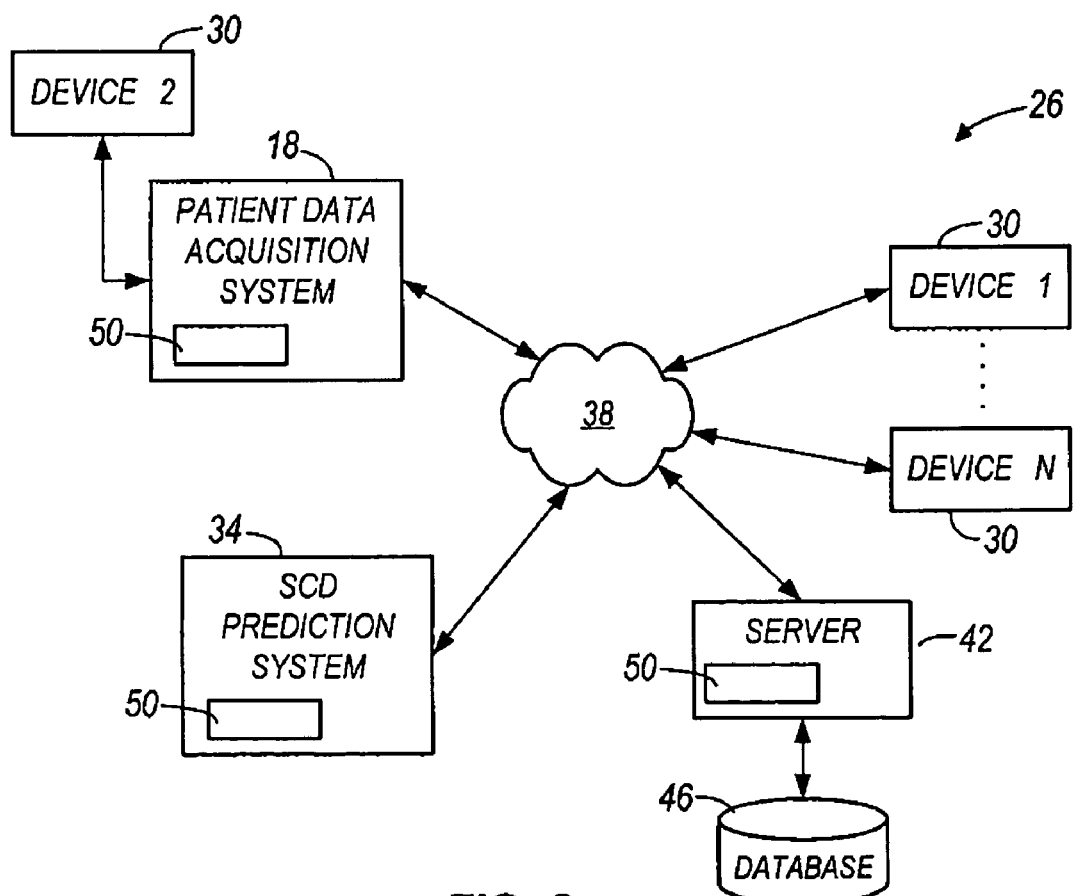
FIG. 2 is a diagram of a sudden cardiac death prediction system according to one embodiment of the invention.

FIG. 2 schematically illustrates a monitoring system 26 according to one embodiment of the invention. The monitoring system 26 can include the patient data acquisition system 18, a device 30 or any number of devices 30, an SCD prediction system 34, and a server 42, each of which can communicate over a network 38. The device(s) 30 can be any suitable medical device or any type of computerized system that can communicate over the network 38. The device(s) 30 can be equipment associated with any one of the cardiology tests described above (e.g., stress test equipment). The device(s) 30 can also be connected to the patient data acquisition system 18. For example, in some embodiments, the device(s) 30 include thermal measurement or gas analysis measurement devices. The SCD prediction system 34 can interface and communicate with the patient data acquisition system 18, the device(s) 30, and any other device in the monitoring system 26. Other embodiments that include fewer or more systems or components than are shown in FIG. 2 are also encompassed by the invention.

The monitoring system 26 can include a database 46 connected to the server 42. The server 42 can generally include an operating system for running various software programs and/or a communications application. In particular, the server 42 can include a software program(s) 50 that can communicate with the patient data acquisition system 18 and/or the device(s) 30 via the network 38. The software program(s) 50 can be manipulated by one or more computer terminals (not shown) and/or other suitable medical equipment to acquire, enter, review, analyze, and save information and/or patient data. The patient data analysis system 18, the device(s) 30, and the SCD prediction system 34 can use a single server and database as is known in the art; however, additional servers and databases may also be used. The database 46 can store information received from the patient data acquisition system 18, the device(s) 30, and the SCD prediction system 34, such as patient data, raw data, analyzed data, processed data, ECGs, respiration data, stress ECGs, echocardiograph images, nuclear images, X-ray images, ECG patterns, image patterns, decision support, mathematical equations, measurements, reports, diagnoses, tables, etc.

The network 38 can be built according to any networking technology or topology or combinations of technologies and topologies and may include multiple sub-networks. Connections between the patient data acquisition system 18, the device(s) 30, and the SCD prediction system 34 and the server 42 can be made through local area networks ("LANs"), wide area networks ("WANs"), public switched telephone networks ("PSTNs"), Intranets, the Internet, and/or any other suitable networks. In a hospital or medical care facility, communication in the monitoring system 26 can be conducted through the Health Level Seven ("HL7") protocol with any version and/or other required protocol. HL7 is a standard protocol which specifies the implementation of interfaces between two computer applications (sender and receiver) from different vendors for electronic data exchange in health care environments. HL7 allows health care institutions to exchange key sets of data from different application systems. Specifically, HL7 defines the data to be exchanged, the timing of the interchange, and the communication of errors to the application. The formats are generic in nature and must be configured to meet the needs of the two applications involved.

The two-way arrows in FIG. 2 represent two-way communication and information transfer between the network 38 and the patient data acquisition system 18, the device(s) 30, and the SCD prediction system 34 and server 42. However, the monitoring system 26 may also include components that are only capable of one-way communication with the network 38 (either one-way reception or transmission of information and/or data).

The SCD prediction system 34 can include a computer terminal (not shown) or other user interface device adapted to be accessed by the medical personnel to determine and/or predict whether a patient is subject to sudden cardiac death.

The SCD prediction system 34 can access the data available for the patient 10 from the patient data acquisition system 18 and the device(s) 30 and the database 46 in order to evaluate various combinations of criteria (e.g., typical ECG measurements, respiration, ejection fraction, wall motion abnormalities, heart rate variability, heart rate turbulence, QRS duration, signal averaged ECG, rhythm abnormalities, T-wave alternans, ST/T measurements, intermittent or chronic atrial fibrillation, etc) and to generate a single medical report. The single medical report can use a combination of parameters and measurements to provide a prediction of sudden cardiac death.

In some cases, the patient 10 may have had a previous heart attack or myocardial infarction, (i.e., a heart attack caused by blockage of a portion of the coronary artery which supplies blood to the heart muscle). As a result of the blockage, a portion of the heart muscle does not receive blood and therefore becomes scarred and diseased. The SCD prediction system 34 can acquire data available for the patient 10 from tests performed before or after the patient 10 experienced a heart attack. If the test data was not electronically stored at the time, but is in paper form, the data can be scanned into or otherwise captured by the SCD prediction system 34, such that the SCD prediction system 34 can analyze differences in the patient's heart condition when making measurements and calculations and providing the single medical report and sudden cardiac death prediction.

Figure 3:
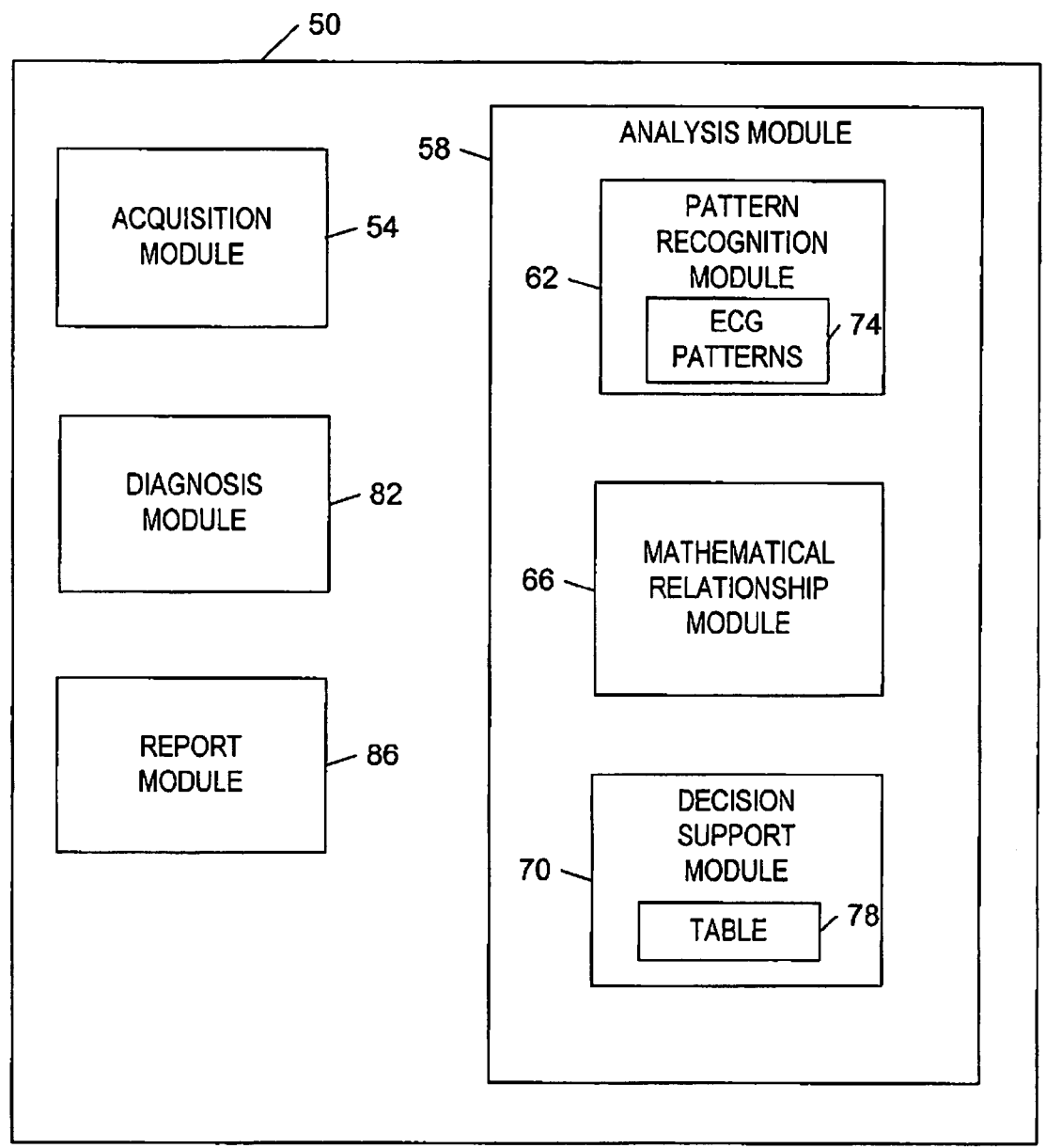
FIG. 3 is a schematic diagram of a software program for use in the sudden cardiac death prediction system of FIG. 2.

As noted, the SCD prediction system 34 can include software program(s) 50 and/or hardware that are stored or included in a server or piece of computer equipment connected to the network 38. However, in some embodiments, all or any suitable portion of the software program(s) 50 and hardware can be stored or included in the patient data acquisition system 18. Alternatively, as shown in FIG. 2, the software program(s) 50 can be stored in the server 42 connected to the network 38 and the database 46, but separate from the patient data acquisition system 18 and the SCD prediction system 34 (which generates the single medical report). As shown in FIG. 3, the software program(s) 50 can include an acquisition module 54, which operates to acquire the patient data from the patient data acquisition system 18 and any data linked to the patient 10 from the device(s) 30 and the database 46. The patient data can include measurements, raw data, unanalyzed data, analyzed data, medical personnel conclusions, images, charts, graphs, identified abnormalities, normal and abnormal ranges, patient identifiers (name, age, sex, weight, race), patient history (cholesterol level, diabetes, family history, smoking, blood pressure, obesity), symptoms, dates of reports and tests, identification of prescribing, attending and reading physicians, etc.

The software program(s) 50 can also include an analysis module 58, which can analyze the acquired data for the patient 10. The analysis module 58 can include a pattern recognition module 62, a mathematical relationship module 66, a decision support module 70, and any additional modules necessary to analyze the acquired data.

The pattern recognition module 62 can include stored ECG patterns 74 with ECGs having known or assigned conditions and diagnoses. The pattern recognition module 62 can provide ECG measurements based on the similarities and differences between the patient's ECGs and the stored ECG patterns 74.

The mathematical relationship module 66 can perform mathematical computations on various parameter values (e.g., heart rate, respiration, typical ECG measurements, etc.) and/or combinations of parameter values to generate mathematical measurements that can be compared to acceptable numbers and/or ranges stored in or accessed by the decision support module 70 (as further discussed below). For example, the mathematical relationship module 66 can be used to determine if the patient 10 has sleep apnea. The mathematical relationship module 66 can also perform correlation and logistic regression analyses to determine a relationship between sleep apnea, SCD, and/or stroke.

The decision support module 70 can include a table 78 of ranges. The ranges can indicate various levels of the progression of heart disease for each parameter value. The ranges can also correlate to the mathematical measurements from the mathematical relationship module 66 and/or ECG measurements from the pattern recognition module 62.

The software program 50 can also include a diagnosis module 82, which can provide a medical diagnosis and/or an SCD risk score based on the analyses performed by the pattern recognition module 62, the mathematical relationship module 66, and/or the decision support module 70. The medical diagnosis can also include an indication of any likely relationship between sleep apnea and SCD, recommended medical treatments or follow-up tests, or an indication that the data was inconclusive. The SCD risk score can identify the level of susceptibility of the patient 10 to sudden cardiac death and the parameters and/or provide the measurements that contributed to the SCD risk score. For example, the SCD prediction system 34 can provide a high SCD risk score if the patient has sleep apnea, an ejection fraction less than 30%, the patient had a prior heart attack (as defined by wall motion abnormality or clinical condition), and/or the patient is experiencing one or more of the following: the QRS duration is greater than 120 ms, the signal averaged ECG is greater than 140 ms, heart rate variability is abnormal, T-wave alternans are abnormal, or the heart rate turbulence is abnormal. Other determinations of sudden cardiac death using more or fewer parameters (including parameters not described herein) can be used and fall within the scope of the invention.

The software program 50 can also include a report module 86, which can provide a single or multiple medical reports that combine multiple independent tests (having multiple parameters such as ECG and respiration). The medical reports can include the SCD risk score, the specific measurements that contributed to the SCD risk score, the ECG and respiration measurements, any image measurements, any mathematical measurements, the acceptable ranges for each parameter used to calculate the SCD risk score, a medical diagnosis (with any recommended treatment, as appropriate), graphs, charts, trends, ECGs, images with ECG indices, images identifying locations of problems, etc. The reporting module 86 can generate a single or multiple medical reports to be displayed on the computer terminal screen or adapted to be printed at a printer.

Figure 4:
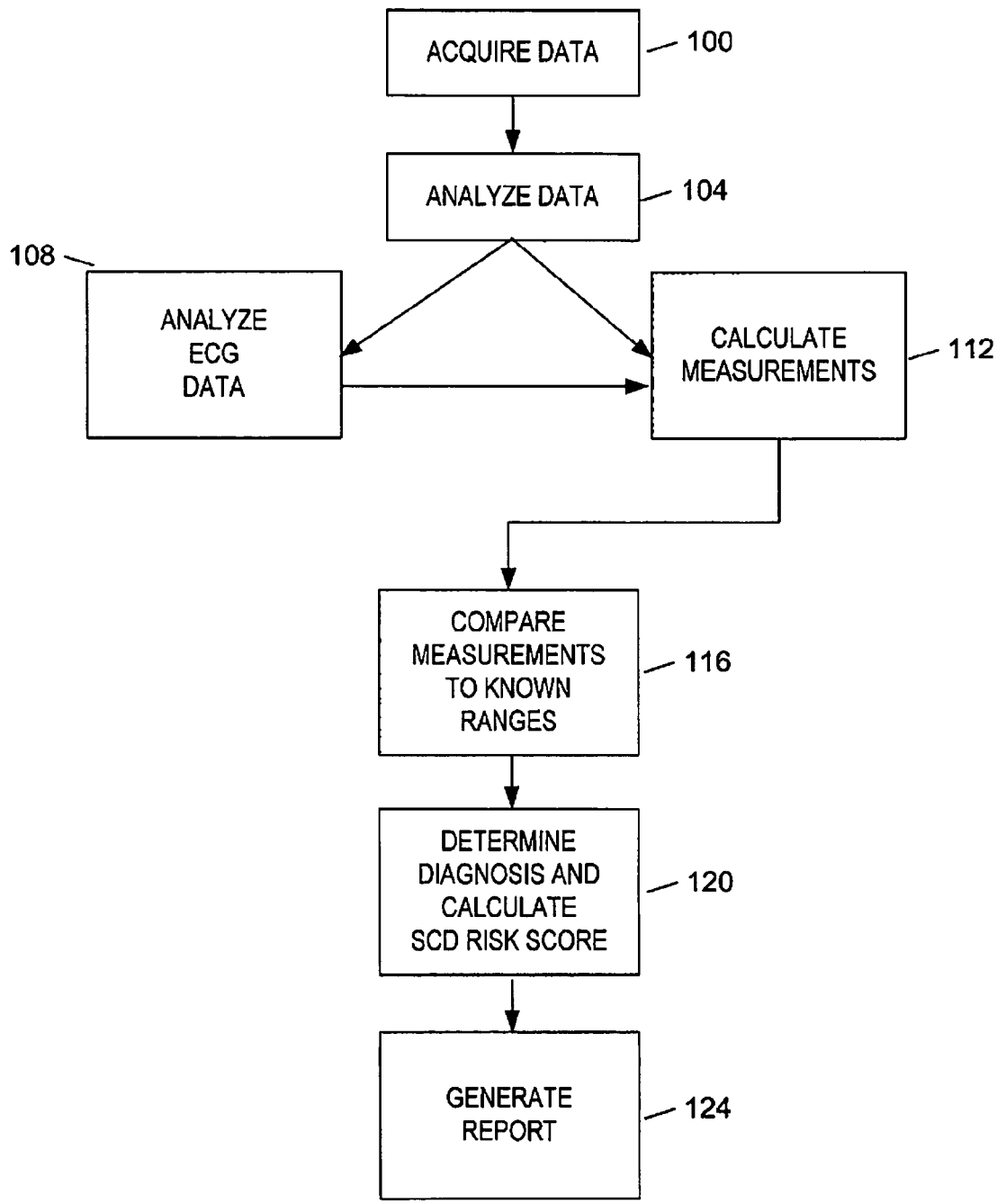
FIG. 4 is a flow chart illustrating the operation according to one embodiment of the invention of the sudden cardiac death prediction system of FIGS. 2 and 3.

According to one embodiment of the method of the invention, as shown in FIG. 4, the SCD prediction system 34 can activate the software program 50 to acquire (at step 100) data for the patient 10 with the acquisition module 54. In some embodiments, the acquisition module 54 can communicate with and acquire the data from the patient data acquisition system 18, the device(s) 30, and/or the database 46 through the network 38.

The analysis module 58 can receive and analyzed (at 104) the patient data. The patient's ECG data can be transmitted to the pattern recognition module 62 for analysis (at 108), such as a comparison with stored ECG patterns 74 having known conditions and diagnoses. The ECG measurements, including the similarities and differences between the patient's ECGs and the stored ECG patterns 74 can be detected and saved. The various parameter values obtained during the various cardiac tests can be transmitted to the mathematical relationship module 66. The mathematical relationship module 66 can calculate (at 112) mathematical measurements based on any single parameter value and/or a combination of parameter values.

The decision support module 70 can receive the mathematical measurements and the ECG measurements. The decision support module 70 can correlate or compare (at 116) the mathematical measurements and the ECG measurements to ranges to determine the patient's level of heart disease.

The diagnosis module 82 can receive the mathematical measurements, the ECG measurements, and the correlation data from the decision support module 70, and can determine a diagnosis and calculate (at 120) the SCD risk score for the patient.

The diagnosis and/or SCD risk score and any other suitable data can be transmitted to the report module 86. The report module 86 can generate (at 124) at least one or more reports that combine at least respiration and ECG measurements for an indication of sudden cardiac death. The reports can be configured for display at a computer terminal and/or printing at a printer.

Various features and advantages of the invention are set forth in the following claims.

What is claimed is:

1. A method of predicting sudden cardiac death in a patient being monitored for sleep apnea, the method comprising:
    acquiring respiration data and electrocardiogram data from the patient;
    analyzing the respiration data and the electrocardiogram data to determine a correlation between sleep apnea and sudden cardiac death; and
    comparing the electrocardiogram data to stored electrocardiogram patterns to determine an electrocardiogram measurement.

2. The method of claim 1 and further comprising analyzing the electrocardiogram data for at least one of heart rate variability, heart rate turbulence, QRS duration, ST/T measurements, ventricular late potentials, and T-wave alternans.

3. The method of claim 1 and further comprising acquiring and analyzing at least one of ejection fraction data and wall motion abnormality data.

4. The method of claim 1 and further comprising acquiring respiration data with at least one of impedance measurements, acoustic measurements, thermal measurements, and gas analysis measurements.

5. The method of claim 1 and further comprising comparing the electrocardiogram measurement to a range to determine an electrocardiogram correlation.

6. The method of claim 1 and further comprising comparing the respiration data to a range to determine a respiration correlation.

7. The method of claim 1 and further comprising determining a mathematical measurement based on a parameter value.

8. The method of claim 7 and further comprising comparing the mathematical measurement to a range to determine a mathematical correlation.

9. The method of claim 1 and further comprising determining a diagnosis based on at least one of an electrocardiogram correlation, a respiration correlation, and a mathematical correlation.

10. The method of claim 1 and further comprising calculating a sudden cardiac death risk score based on at least one of an electrocardiogram correlation, a respiration correlation, and a mathematical correlation.

11. The method of claim 10 and further comprising including at least one of electrocardiogram data, respiration data, and the sudden cardiac death risk score in a single report.

12. The method of claim 1 and further comprising determining a correlation between sleep apnea, sudden cardiac death, and stroke.

13. A computer program embodied by a computer readable medium capable of being executed by a computer, the computer program comprising:
    an acquisition module that acquires electrocardiogram data and respiration data;
    an analysis module that analyzes the electrocardiogram data and the respiration data and calculates a plurality of measurements;
    a diagnosis module that provides a medical diagnosis including a relationship between sleep apnea and sudden cardiac death based on the plurality of measurements; and
    a report module that provides a report including the relationship between sleep apnea and sudden cardiac death.

14. The computer program of claim 13 wherein the report module provides a report including at least one of electrocardiogram data, an electrocardiogram measurement, respiration data, a respiration measurement, a diagnosis, a recommended treatment, a recommended follow-up test, a sudden cardiac death risk score, a range, a patient identifier, a patient history, and a physician identifier.

15. The computer program of claim 13 wherein the analysis module analyzes the electrocardiogram data for at least one of heart rate variability, heart rate turbulence, QRS duration, ST/T measurements, ventricular late potentials, and T-wave alternans.

16. The computer program of claim 13 wherein the acquisition module acquires at least one of ejection fraction data and wall motion abnormality data.

17. The computer program of claim 13 wherein the acquisition module acquires respiration data with at least one of impedance measurements, acoustic measurements, thermal measurements, and gas analysis measurements.

18. The computer program of claim 13 wherein the analysis module includes a pattern recognition module, the pattern recognition module accessing electrocardiogram patterns.

19. The computer program of claim 13 wherein the analysis module includes a mathematical relationship module that determines if a patient has sleep apnea and determines the relationship between sleep apnea and sudden cardiac death.

20. The computer program of claim 13 wherein the analysis module includes a decision support module that determines the medical diagnosis and a sudden cardiac death risk score.

21. A device for monitoring sleep apnea and a risk of sudden cardiac death for a patient, the device comprising:
    at least one electrocardiogram electrode that can be attached to the patients to acquire electrocardiogram data;
    at least one respiration electrode that can be attached to the patient to acquire respiration data; and
    a patient data acquisition system that receives the electrocardiogram data and the respiration data and determines a correlation between sleep apnea and a risk of sudden cardiac death.

22. The device of claim 21 wherein the patient data acquisition system analyzes the electrocardiogram data for at least one of heart rate variability, heart rate turbulence, QRS duration, ST/T measurements, ventricular late potentials, and T-wave alternans.

23. The device of claim 21 wherein the patient data acquisition system acquires and analyzes at least one of ejection fraction data and wall motion abnormality data.

24. The device of claim 21 wherein the patient data acquisition system acquires respiration data with at least one of impedance measurements, acoustic measurements, thermal measurements, and gas analysis measurements.

25. The device of claim 21 and further comprising a portable housing that can be worn by a patient, the at least one electrocardiogram electrode and the at least one respiration electrode being connectable to the portable housing, the patient data acquisition system being included in the portable housing.

26. A device for monitoring sleep apnea and a risk of sudden cardiac death for a patient, the device comprising:
- means for acquiring electrocardiogram data from the patient;
- means for acquiring respiration data from the patient; and
- means for determining a correlation between sleep apnea and a risk of sudden cardiac death.

27. A device for monitoring sleep apnea and a risk of sudden cardiac death for a patient, the device comprising:
- at least one electrode that can be attached to the patient to acquire electrocardiogram data and respiration data; and
- a patient data acquisition system that receives the electrocardiogram data and the respiration data and determines a correlation between sleep apnea and a risk of sudden cardiac death.

* * * * *